(12) United States Patent
Bunting et al.

(10) Patent No.: US 8,663,162 B2
(45) Date of Patent: Mar. 4, 2014

(54) TATTOO REMOVAL SYSTEM

(75) Inventors: Alan Bunting, Loxahatchee, FL (US); Jack Savage, Sandy, UT (US)

(73) Assignee: Rejuvatek Medical Inc., Sandy, UT (US)

( * ) Notice: Subject to any disclaimer, the term of this patent is extended or adjusted under 35 U.S.C. 154(b) by 0 days.

(21) Appl. No.: 13/575,931

(22) PCT Filed: Jan. 19, 2011
(Under 37 CFR 1.47)

(86) PCT No.: PCT/US2011/000101
§ 371 (c)(1),
(2), (4) Date: Jul. 27, 2012

(87) PCT Pub. No.: WO2012/099563
PCT Pub. Date: Jul. 26, 2012

(65) Prior Publication Data
US 2013/0123746 A1    May 16, 2013

(51) Int. Cl.
*A61M 5/00* (2006.01)
*A61B 17/20* (2006.01)
*A61M 37/00* (2006.01)
*A61M 31/00* (2006.01)

(52) U.S. Cl.
USPC ............................ 604/116; 604/46; 604/506

(58) Field of Classification Search
USPC ............ 604/28, 506, 46, 116, 117, 289, 306, 604/307; 606/116, 186
See application file for complete search history.

(56) References Cited

U.S. PATENT DOCUMENTS

| | | | |
|---|---|---|---|
| 2,840,076 | A | 6/1958 | Robbins |
| 4,798,582 | A | 1/1989 | Sarath et al. |
| 5,012,797 | A | 5/1991 | Liang et al. |
| 5,833,649 | A | 11/1998 | Atef |
| 6,505,530 | B2 | 1/2003 | Adler et al. |
| 6,626,865 | B1 * | 9/2003 | Prisell ........................ 604/116 |
| 6,855,133 | B2 | 2/2005 | Svedman |
| 7,179,253 | B2 | 2/2007 | Graham et al. |
| 7,314,470 | B2 | 1/2008 | Malodobry |
| 7,618,429 | B2 | 11/2009 | Mulholland |
| 7,905,854 | B2 | 3/2011 | Hazut et al. |
| 2003/0208167 | A1 | 11/2003 | Prausnitz et al. |
| 2005/0010236 | A1 | 1/2005 | Frister |
| 2006/0258992 | A1 | 11/2006 | Stoop |

(Continued)

FOREIGN PATENT DOCUMENTS

| | | |
|---|---|---|
| EP | 1514574 A2 | 9/2001 |
| EP | 1514574 A3 | 9/2001 |

(Continued)

OTHER PUBLICATIONS

PCT International Search Report and Written Opinion, PCT/US2011/000101 dated Oct. 17, 2011.

*Primary Examiner* — Manuel Mendez
*Assistant Examiner* — Rebecca E Eisenberg
(74) *Attorney, Agent, or Firm* — TraskBritt

(57) ABSTRACT

Described is a system and associated materials and methods for delivering a fluid to a subject's skin, e.g., for tattoo removal. In one embodiment, the fluid is provided in a continuous flow by associating the fluid with a pump. In another embodiment, a disposable template is provided that allows for precise and ideal placement of eschar-inducing material fluid for, for example, tattoo removal.

8 Claims, 8 Drawing Sheets

(56) References Cited

U.S. PATENT DOCUMENTS

| | | |
|---|---|---|
| 2007/0156095 A1 | 7/2007 | Hazut et al. |
| 2008/0033470 A1 | 2/2008 | Kluge |
| 2008/0077170 A1 | 3/2008 | Kluge et al. |
| 2008/0208235 A1 | 8/2008 | Ulmer et al. |
| 2008/0247637 A1 | 10/2008 | Gildenberg |
| 2008/0262416 A1 | 10/2008 | Duan et al. |
| 2009/0125050 A1 | 5/2009 | Dixon |
| 2010/0023003 A1 | 1/2010 | Mulholland |
| 2010/0082019 A1 | 4/2010 | Neev |
| 2010/0121259 A1* | 5/2010 | Lutski et al. .............. 604/22 |

FOREIGN PATENT DOCUMENTS

| | | |
|---|---|---|
| EP | 1514574 B1 | 9/2001 |
| EP | 1709989 A1 | 4/2005 |
| JP | 2003339875 A | 12/2003 |
| WO | 8912440 A1 | 12/1989 |
| WO | 2005020828 A1 | 3/2005 |
| WO | 2005027868 A1 | 3/2005 |
| WO | 2006106062 A1 | 10/2006 |
| WO | 2008120204 A1 | 10/2008 |
| WO | 2012099563 A1 | 7/2012 |

\* cited by examiner

TATTOO REMOVAL SYSTEM

TECHNICAL FIELD

Generally, the disclosure relates to a system and associated devices, materials, and methods for the removal of tattoos. More specifically, described is a system and associated materials and methods for delivering a fluid into a subject's skin, e.g., for tattoo removal. In one embodiment, the fluid is provided in a continuous flow by associating the fluid, e.g., with a pump for delivery of the fluid through a needle cartridge. In another embodiment, a disposable template is described that allows for precise and ideal placement of eschar-inducing material fluid for, for example, tattoo removal. Besides tattoo removal, the system and associated methods may be used for reducing stretch marks and the appearance of other scars.

BACKGROUND

Including people who have "permanent makeup," it is estimated that about 10% of the U.S. population has at least one tattoo. Despite the increasing popularity of tattoos, their removal can be equally desired (e.g., due to a poor design or artwork, change of partners, career concerns, or social stigma). Anecdotally, over one-half of the people who have a tattoo have considered having it removed.

Laser treatments are the currently most accepted method of removing a tattoo. While generally better than other methods (e.g., excision or dermal abrasion of the tattoo), tattoo removal by laser treatment remains problematic. Besides being relatively expensive, exposure to high-intensity laser light degrades a tattoo's pigments into smaller chemical components, which compounds are to be cleared by the body. These compounds are left to be metabolized and excreted by the body with unknown consequences.

Laser light treatment can also generate significant heat that makes the treatment painful and may cause its own scarring. In addition, laser light works best with only a limited range of colors (e.g., black, blue, and red pigments). Many other colors in widespread use respond poorly to the treatment. Besides only removing a small range of colors, such treatment requires an average of 10 separate sessions for optimal outcomes, and leaves behind a visible result (e.g., a scar or residual colors).

Instruments for the intradermal injection of fluids are known. (See, e.g., U.S. Pat. No. 2,840,076 to Robbins, Jun. 24, 1958, the contents of the entirety of which are incorporated herein by this reference). Robbins describes a surgical instrument for subcutaneous injection of liquefied pigments, medicinal, or cosmetic materials that includes means for controlling the depth of application of such liquefied materials, wherein the depth of the application can be rapidly varied.

Devices for removing a tattoo are also known. (See, e.g., U.S. Pub. No. 2008/020835 A1 to Ulmer et al., Aug. 28, 2008, the contents of the entirety of which are incorporated herein by this reference).

DISCLOSURE

Described is a non-laser tattoo removal system and associated methods of treatment (e.g., a cosmetic process). In the method, first, the skin area around the tattoo is cleaned (which cleaning may include shaving the tattoo). Utilizing a template having apertures therefore adapted for such use, "dots" are marked upon the subject's skin about the tattoo, e.g., with a skin marker. The template is removed, and an eschar-inducing material (e.g., an injectable liquid containing an alpha hydroxy acid in an amount sufficient to dissolve tattoo pigment and form an eschar in the subject's skin) is injected with a needle into a subject's tattoo into the evenly spaced dots (i.e., areas of the skin corresponding to the apertures in the template). During the process, the placement of the needle acts to deliver the eschar-inducing material to the skin to thus disrupt the pigments in the skin that form the tattoo. The eschar-inducing material thus placed releases the pigments from the deeper tissues of the skin, dissolving them somewhat, and an eschar coagulates and forms from the pigments and local tissue.

This procedure creates a temporary eschar, which brings the tattoo's pigments to the skin's surface for removal, which eschar, when separated from the skin, and after the skin subsequently heals, leaves the underlying tissues more clear of tattoo pigment. After allowing time for sufficient maturation of the healing treated skin to take place (e.g., for six (6) to twelve (12), e.g., eight (8), weeks), the process is repeated. Approximately, four such treatment sessions are generally required, with a new template being "shifted" or offset to a position where the eschar-inducing fluid is placed into areas of the skin not previously treated. The process is repeated until the tattoo is removed. In essence, this is a forced leaching method.

The described procedure has minimal discomfort and results in minimal scarring. Each treatment session typically takes about thirty (30) minutes in which small circles or "dots" are created over the surface of the tattoo as determined by the template. The spaces between the dots are not filled in, and are treated during the next session. This spacing strategy minimizes the trauma to the skin and reduces visible scar formation. An eschar forms after each treatment and comes off in about two (2) weeks.

As previously identified, the process requires a series of treatments spaced out over time. The treatments are usually, on average, about eight (8) weeks apart but can be twelve (12) to sixteen (16) weeks apart, and an average number of treatments is at least four to eight, depending on the size of the tattoo, for maximal clearing of the tattoo. The results after each treatment will determine how many treatments are needed.

The described system offers numerous advantages over laser tattoo removal including a reduced cost. Without using a laser, the cost of tattoo removal treatments drops by about 50% or even more. While more affordable treatments are appealing in and of themselves, they would be meaningless if it were not at least as effective as laser treatments. The described treatment may be just as effective as laser treatment, if not more so, since it can treat all colors including the most exotic hues and pigment blends, such as green, yellow, and orange. It is truly a "color blind" treatment method because its effectiveness is not based on color-based absorption (unlike laser light).

In certain embodiments, a tattoo machine is used to deliver the eschar-inducing material under the skin using the associated needle cartridge of a tattoo machine, wherein the eschar-inducing material is administered in a predetermined pattern of closely spaced circles. Preferably, the tattoo machine has been adapted so that the eschar-inducing material is delivered in a continuous flow via a pump or pressurized system associated with the reservoir of eschar-inducing material.

DETAILED DESCRIPTION

Figure 1:
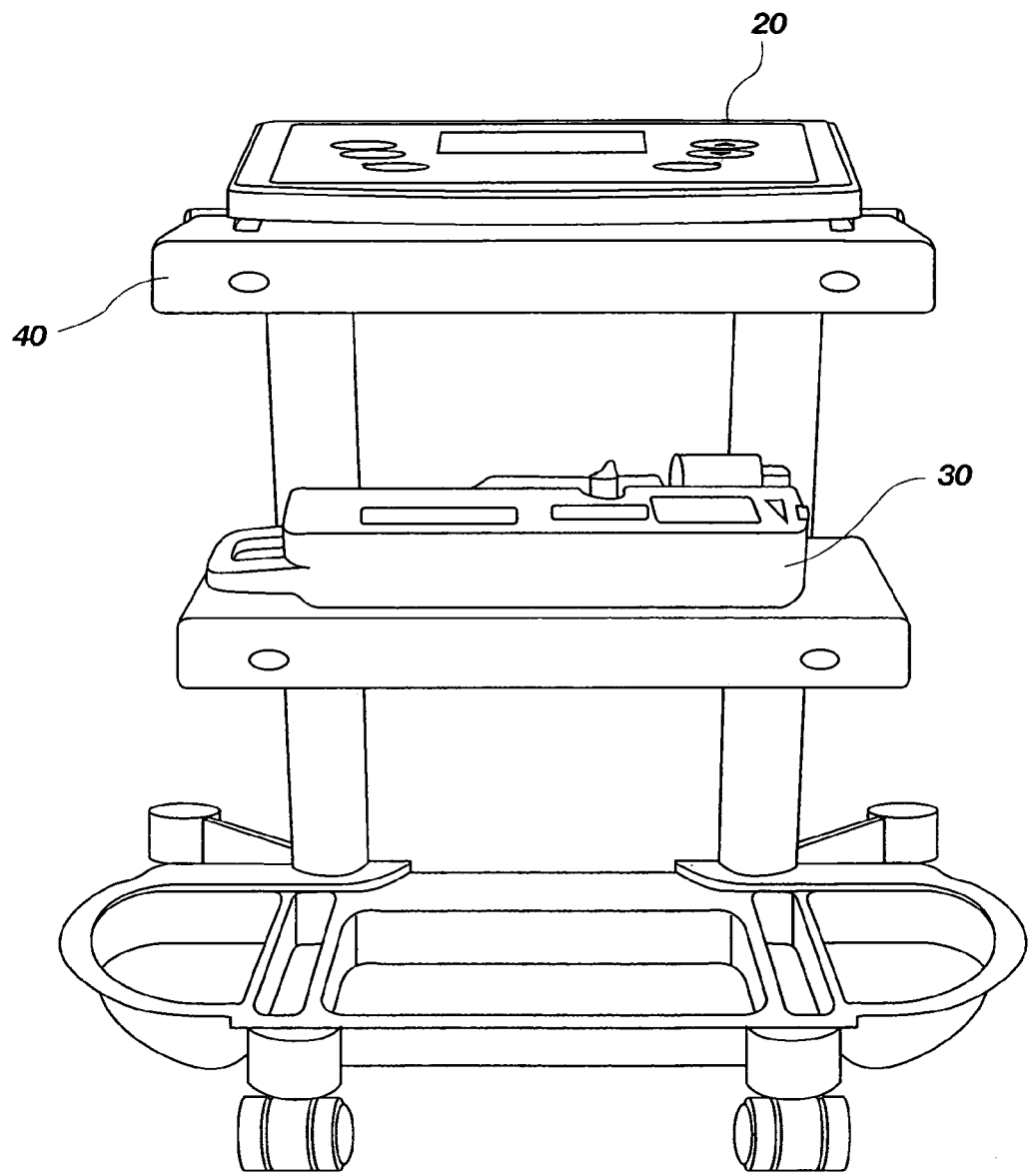
FIG. 1 depicts a workstation with a portion of the system described herein.

A system for use with the described methods (FIG. 1) typically includes a console 20, hand piece wand (not shown in FIG. 1), fluid delivery system 30, instruction manual (not shown in FIG. 1), workstation 40, and disposable supplies such as the eschar-inducing material (not shown in FIG. 1).

Figure 2:
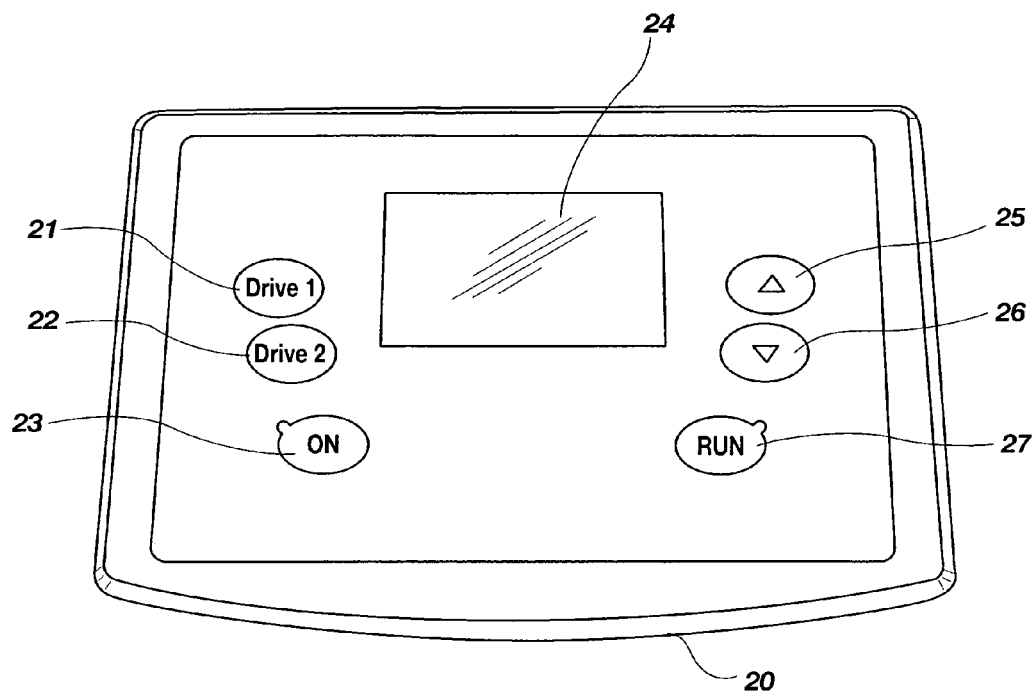
FIG. 2 depicts a console for use with the system.

The console 20 depicted in FIG. 2 includes a first drive selection 21, second drive selection 22, power on switch 23, display screen 24, motor speed increase switch 25, motor decrease switch 26, and motor start 27. The hand piece wand (not shown in FIG. 2) and a foot pedal control (not shown in FIG. 2) are in operable communication with the console 20.

Figure 3:
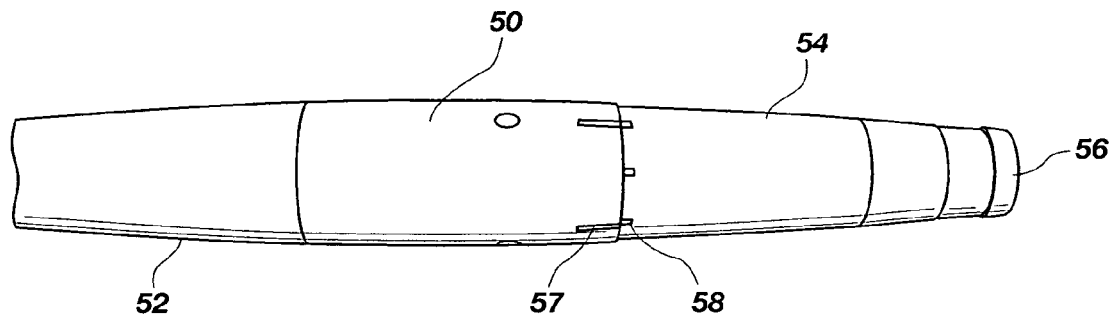
FIG. 3 depicts a hand piece wand for use with the system.
Figure 4:
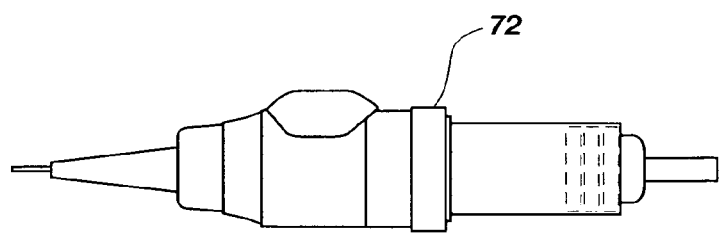
FIG. 4 depicts a needle cartridge for use with the system.

The hand piece wand 50 depicted in FIG. 3 is typically an elongate cylindrical metal or plastic member shaped for holding with the human hand that includes an upper barrel 52, lower barrel 54, and a threaded inner portion 56 for receiving a needle cartridge (FIG. 4) by corresponding threaded attachment between the hand piece wand and needle cartridge. Both the upper and lower barrels have corresponding gradation marks 57, 58 for determining needle depth.

A cartridge needle has needles and tip as one assembly. The needles (e.g., three to seven of them) are molded into a plastic bar and not soldered together. The tip of the needle cartridge is molded in so as to guide and hold the needles into the specified configuration. The back of the rod rides in a seal that is retained in the needle cartridge so as not allow any fluid (or pigment) flow back into the hand piece wand. Needle cartridges (FIG. 4) such as seven-membered tattoo needle cartridges are commercially available from. e.g., MT.DERM GmbH of Berlin, Del. Needle cartridges are typically labeled with the lot number, date of manufacture and use-by date. The lot number helps with the clear identification of the batch and has been issued by the manufacturer in case of any problems. The lot number should be noted in the subject's file.

Figure 5:
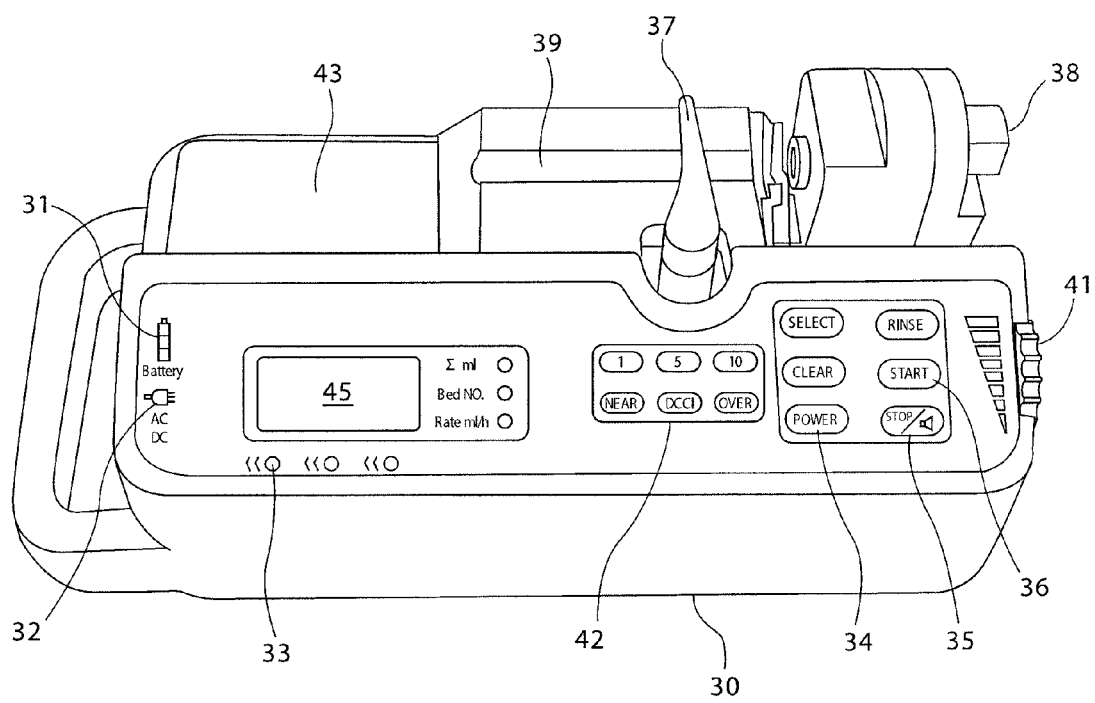
FIG. 5 depicts a fluid delivery system for use with the system.

The fluid delivery system 30 depicted in FIG. 5 is a syringe pump, and includes a battery capacity indicator 31, power light 32, fluid delivery indicator 33, power on/off switch 34, fluid delivery off switch 35, start delivery on switch 36, syringe retainer lock 37, piston release button 38, syringe cradle 39, fluid delivery control and confirmation knob 41, syringe size selector 42, and quick setup instructions 43. Syringe pumps adaptable for use with the system are commercially available (e.g., from E Power Electronics and Science Co. Ltd of Changsha, Hunan Province, PRC).

Figure 6:
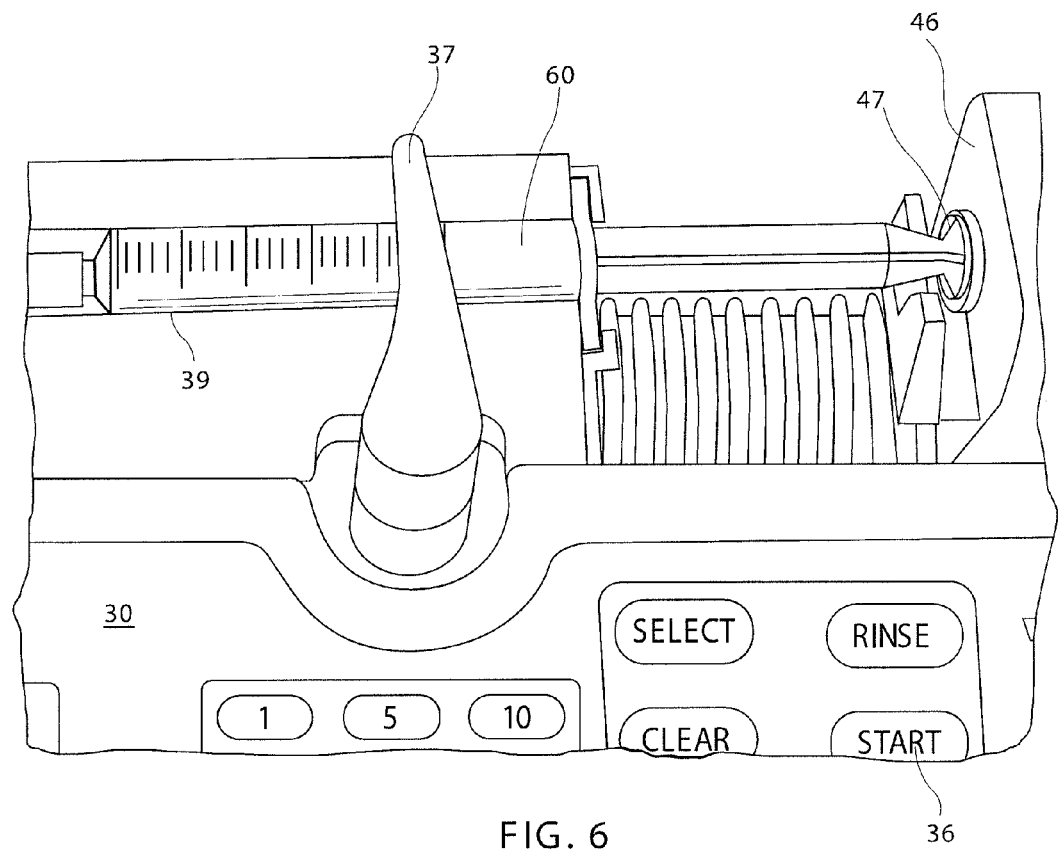
FIG. 6 depicts a close up of the syringe placed with the fluid delivery system for use with the system.
Figure 7:
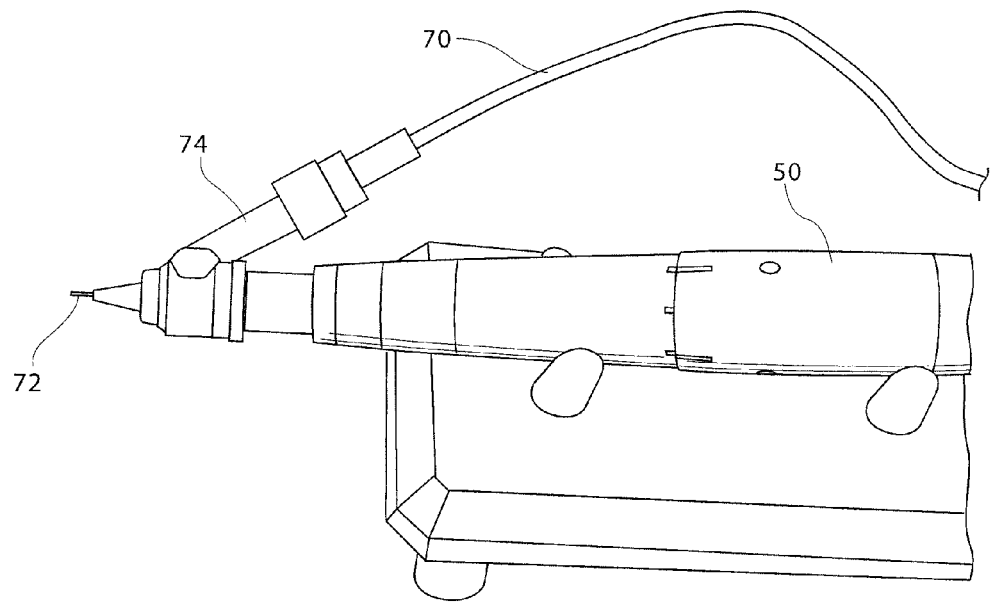
FIG. 7 depicts a close up of the eschar-inducing material fluid tubing in fluid communication with the needle cartridge for use with the system.

In operation, a syringe 60 filled with eschar-inducing material fluid is placed in the syringe cradle 39, and the syringe retainer lock 37 is placed over the syringe (FIG. 6). The piston of the syringe 60 has thus been extended and associated with (e.g., linked and locked with) a piston that forms part of and is controlled by the fluid delivery system. A fluid line 70 (e.g., appropriately sized polymeric tubing) extends from the delivery end of the syringe 60 and extends to and is connected with the hand wand piece 50 (FIG. 7) and is in fluid communication with the associated needle assembly 72 for delivering eschar-inducing material fluid to the needles 72.

The fluid or eschar-inducing material used in the system can include lactic acid, sodium hydrazine, kitchen salt, amino acids, fruit acids, oxidants, or acids such as an alpha hydroxy acid or acids. The fluid will typically be in the form of a diluted aqueous (5 to 60% (w/w)) solution, dispersion, or emulsion. Glycolic acid, lactic acid, citric acid, and mixtures of any thereof are typical useful acids. U.S. Patent Application Publication No. 2006/0258992 to Stoop (Nov. 16, 2008), the contents of which are incorporated herein by this reference, discloses the use of an aqueous solution of an alkali chloride (e.g., 10-20% NaCl by weight) having a pH less than 7 and other tattoo-removing substances. In certain embodiments, the fluid may also include buffers, a bleaching agent, such as a peroxide (e.g., $H_2O_2$(aq) or carbamoyl peroxide). In certain embodiments, the fluid can include one or more buffers, local anesthetics, antibiotics, antiseptics, and/or soothing agents.

System Operation

To operate the depicted system, switch the console 20 on by pressing the "ON" switch 23. An indicator lamp lights up next to the switch 23, and the display screen 24 shows the "welcome" introduction. Next, the hand piece wand 50 is switched on by pressing a "DRIVE" button 21. Pressing the drive button 21 again turns the hand piece wand 50 off. It is also possible to operate the hand piece wand 50 with a foot switch (not shown) associated with the system. For instance, depressing the footswitch once will turn the hand piece wand on. Pressing it again switches it off.

While the device is switched on, the penetration frequency can be adjusted in 20 cycle increments from 50 to 150 cycles by pressing the buttons 25 (faster) and 26 (slower). The selected frequency is shown in the display 24.

When treating subjects, the hand piece wand 50 is held in an almost vertical, down position. It is important to position the tattoo in a manner that allows the hand piece wand 50 to be kept in an almost vertical position above it. For other purposes, e.g., when putting the device down during a break or for adjusting or checking the projection of the needle, the needle is kept vertically down in order to keep fluid from running back into the hand piece mechanism 50.

The depth of needle penetration is preferably adjusted while the system is running. Note the gradations 57, 58 on the upper 52 and lower 54 barrels of the hand piece wand. Each increment on the lower section in the depicted hand piece wand corresponds to 0.25 mm needle depth. The depth of needle penetration is "zeroed" before adjustments are made to the needle penetration depth. To zero the needles, the bottom and top barrels of the hand piece wand are held and the upper barrel moved all the way to the right while holding the bottom barrel stationary. This ensures that the needles are fully retracted into the cartridge housing.

With the motor running slowly, the top section of the hand piece wand is rotated to the left until the needles are just visible at the exit point of the needle housing. When the needles are just visible, the top section of the hand piece wand is turned one gradation to the right. This is the zero position.

Each gradation on the lower barrel of the hand piece wand represents a needle depth increase or decrease of ⅛ mm or 0.125 mm. With the motor running, to extend the needles one (1) mm, turn the upper section one complete rotation to the left or eight gradations to the left. To extend the needles two (2) mm, the upper section is turned two complete rotations to the left or sixteen gradations to the left. For 1.5 mm, the rotation is therefore twelve gradations to the left.

Correct needle projection depends on the anatomical location of the tattoo, depth and layering of the tattoo pigment, skin type, and other factors.

To remove the safety cartridge, unscrew the safety cartridge to remove it from the hand piece wand taking care that any fluid does not run back into the hand piece mechanism. A new needle cartridge is used for each subject and every subsequent treatment. The needle cartridges are designed for single use.

To use the fluid delivery system 30, an associated power cord is attached into back of the pump and plugged into an electrical outlet. The power button 34 is pressed and held for three to five seconds to turn the fluid delivery system on.

A treatment syringe, extension tubing set, and barrier sheath are obtained, e.g., from the workstation. The cap is removed from the end of the treatment syringe and the female LUER-LOCK® of the extension set is attached to the syringe 60. Just enough (approx. 1 ml) eschar-inducing material fluid is gently pushed through the tubing line 70 until it begins to exit the end of the male LUER end of the tubing. Pull upward on the syringe retainer lock 37 located on the top center of the infusion pump and rotate it ninety degrees to the left. Place the syringe 60 with the attached tubing 70 into the mounting grooves 39 of the fluid delivery system 30. In the depicted embodiment (FIG. 6), it may be necessary to adjust the large end piece 46 on the right side to adjust it outward or inward to fit the plunger 47 of the syringe 60 into the outer mounting groove. Once the syringe 60 is in place, the syringe retainer lock 37 is lifted and rotated ninety degrees clockwise so that it fits tightly across the top of the syringe 60.

The user ensures that the light on the control panel is on next to the "Rate ml/h" designation adjacent the display 45 (FIG. 5). If not, the associated select button is pushed until it is. Using the control wheel 41 on the right of the fluid delivery system 30, the flow rate is adjusted to about 10.0 ml/hr. For treatment, the rate is then typically reduced to 2-3 ml/hour and the control wheel is pushed 'in' until an audible 'beep' is heard, which saves the setting. The needle cartridge 72 is attached to the hand piece wand 50 by screwing it into the end of the hand piece 50.

The start button 36 is pushed and the user waits until the first drop of fluid starts flowing from the end of the tubing 70. The stop button 35 is pushed to stop the flow of fluid.

A tubing attachment clip 74 (FIG. 7) is obtained. The fluid delivery attachment or clip 74 is fitted onto the needle cartridge 72 making sure that the aperture on the fluid delivery attachment matches the associated aperture on the needle cartridge 72. The male LUER is attached on the end of the tubing 70 to the attachment clip 74 by slipping it into the exposed opening on the attachment clip 74. The hand piece wand 50 may then be placed with the attached tubing 70 through the plastic barrier sheath until the end of the needle cartridge 72 on the hand piece wand 50 exits slightly through the end of the barrier sheath.

The foot control, power cord, and hand piece wand connections may be made into the back of the console 20 for the hand piece wand 50 and the plug power cord into an electrical outlet.

The console 20 is turned on by pressing the on button 23. A light will appear. A window on the center of the console indicates the speed setting for the needle movement per minute. This can be adjusted up to a maximum speed of 150 cycles.

To begin, the start button on the infusion pump is pushed and the foot pedal is depressed to activate the needle cartridge 72. A drop of fluid will start to appear in about ten seconds from the bottom of the needle set 72. The needle cartridge 72 is positioned over the first five (5) mm dot area to be treated and treatment begins.

If the flow rate needs adjusting up or down, let up on the foot pedal, and press the stop button 35 on the delivery pump. Using the control wheel on the right 41, adjust up or down and press the wheel 'in' to save the setting. The flow rate typically does not exceed 20 ml/hr. Press start 36 to continue. Press the stop button 35 when the hand piece wand 50 is not in use for more than thirty (30) seconds. Otherwise, excess eschar-inducing material fluid may overfill the reservoir and may leak down the sides of the needle set.

When the procedure is finished, the power to the infusion pump 30 may be turned off by pressing the power button 34 for about five seconds until it is powered down and the off button on the console 20 pressed to power it off.

The syringe 60, extension set tubing 70, and the needle cartridge 72 from the hand piece wand 50 are then disposed of. The subject should receive a post-treatment homecare package.

Preferred Method

In a method according to the invention, first, risk factors involved in tattoo removal are determined for a subject. Risk factor assessment charts are provided to allow the user (e.g., a physician) to determine whether the subject is a suitable case for treatment. Such charts may be based on the Kirby/Desai scale used in laser tattoo removal.

Next, the anatomical location and qualities of the tattoo are assessed to determine the potential success of the procedure and the propensity for a poor result. For instance, if colors other than blacks and reds are used, such colors are very unlikely to be removed by laser removal. If it is a less distinct and blurred at the margins, the tattoo is likely to be older and deeper. The design and measure of the tattoo is determined as is its maximum dimensions. Preferably, such information is recorded.

Likewise, throughout the procedure, a good quality photograph under the same conditions and from the same position is preferably taken (a) before commencing treatment, (b) at the beginning of each treatment session, and (c) at any unusual event or complication.

On the basis of the history and assessment of the tattoo itself, it is advisable to plan the treatments. Such planning can include determining whether the first session is to be a test patch or a full treatment; how many sessions will likely be required to remove the tattoo; what is the likely interval between treatments; and what scar prevention management (e.g., EPIDERM®) will be utilized between treatments.

The eschar-inducing material delivery device or wand 50 has a needle cartridge 72. The presently preferred needle cartridge contains seven, medical grade, closely packed micro needles. Such a configuration allows for the most efficient trans-epidermal and most superficial dermal injury. The needle units 72 are single use and, after use, should be treated as a biohazard.

The needle depth setting is important to the precision of the process. Most professional tattoos are placed at depths in the dermis of between one (1) and two (2) millimeters. Amateur tattoos, however, typically have highly variable depth profiles due to the random nature of the single point needle penetration and should be apprised accordingly. The needles are preferably adjustable as to their depth setting to 0.25 mm. If the eschar-inducing material delivery needle (or needles) does not penetrate far enough into the dermis, then the depth of total injury to the epidermis and dermis (needle injury and fluid injury depth) will not reach the deepest situated tattoo pigment (tattoo pigment depth). In such a case, the tattoo pigment will not be completely eliminated. However, if the needle is set too deep, the total depth of injury will be equivalent to the full thickness of the skin. In such a case, although all of the pigment may be eliminated, the individual injuries may heal more slowly, form the margins of each dot and have the potential to leave more of a mark or scar.

For needle depth selection, the user should judge the relative depth of injury that any needle setting will produce. For example, in the thick skin of the back, a one (1) mm setting will produce an injury which is more superficial than a one (1) mm setting in the thinner skin of the dorsal forearm. When the user is unsure which needle depth setting may be most appropriate for a particular tattoo, it is best to perform a test patch. Typically, however, a depth setting on the needle of between 0.5 mm and 1.5 mm is utilized. The depth setting is to be less than the estimated full thickness of the skin at this anatomical site.

The user should ensure that the needle unit and the fluid delivery apparatus are set-up correctly and fluid is being delivered to tip before proceeding to treat the subject.

A test patch may be performed upon a subject prior to a formal treatment session. A test patch permits assessment of the needle depth setting required for a full treatment, the subject's tendency to excessive scarring, and anesthetic technique, if any, required for a full session treatment. The test patch may also give an indication of whether there is a tendency toward hypertrophic scarring at this anatomical site. The disadvantage of the test patch is to introduce a time delay into the treatment process.

For the test patch, three treatment dots are created in a row within the tattoo, each dot with a progressively deeper depth needle setting. The user records which depth setting was used with each dot. The dots are allowed to heal and mature. Each dot of the test patch is individually assessed to determine which dot is the most superficial to successfully remove all the pigment.

The site of the tattoo should be cleaned on the morning of the treatment, e.g., in the shower. The tattoo may be washed immediately prior to treatment.

If the area of skin is covered with other than fine vellus hair, it should be shaved. Otherwise the treatment process will be difficult to accomplish. Shaving should take place immediately prior to the procedure in order to minimize the chance of wound infection.

The skin should be prepared, e.g., with an alcohol-based wipe or gel.

Although many subjects tolerate the tattoo removal procedure without supplemental analgesia, some form of analgesia is generally recommended. The hand, fingers, and feet are usually sites at which some form of topical or injectable local anesthetic is useful. Such analgesic requirements include oral NSAIDs, topical anesthetics, EMLA, AMETOP or equivalents, cooling, injection, local infiltration, and regional block. For topical anesthetics, twenty (20) to thirty (30) minutes may be needed before the optimal effect is experienced.

After the procedure, simple oral analgesia for a day is all that is usually required. However, tattoos located on the distal extremities are more likely to become infected than those placed on the head, neck, or body. Prophylactic antibiotics may coincide with the start of treatment.

The actual treatment is conducted by marking a predetermined (by template placement) regular pattern of closely spaced, de-epithelialized circles or dots about and within the tattoo design. After removal of the template from the subject's skin, an eschar-inducing material is dispensed into the skin under these dots. The needles of the needle cartridge 72 deliver the eschar-inducing material to the local area and allow the thus introduced eschar-inducing material to access the tattoo pigment. The eschar-inducing material acts to disrupt the local cells and liberate the tattoo pigment from the skin, thus forming (or "coagulating") an eschar contains the disrupted local tissues and dissolved pigments. Subsequent healing of these treated dots, followed by "in-filling" re-treatment (between the dots) at a suitable time interval, incrementally eliminates the tattoo design.

Figure 8:
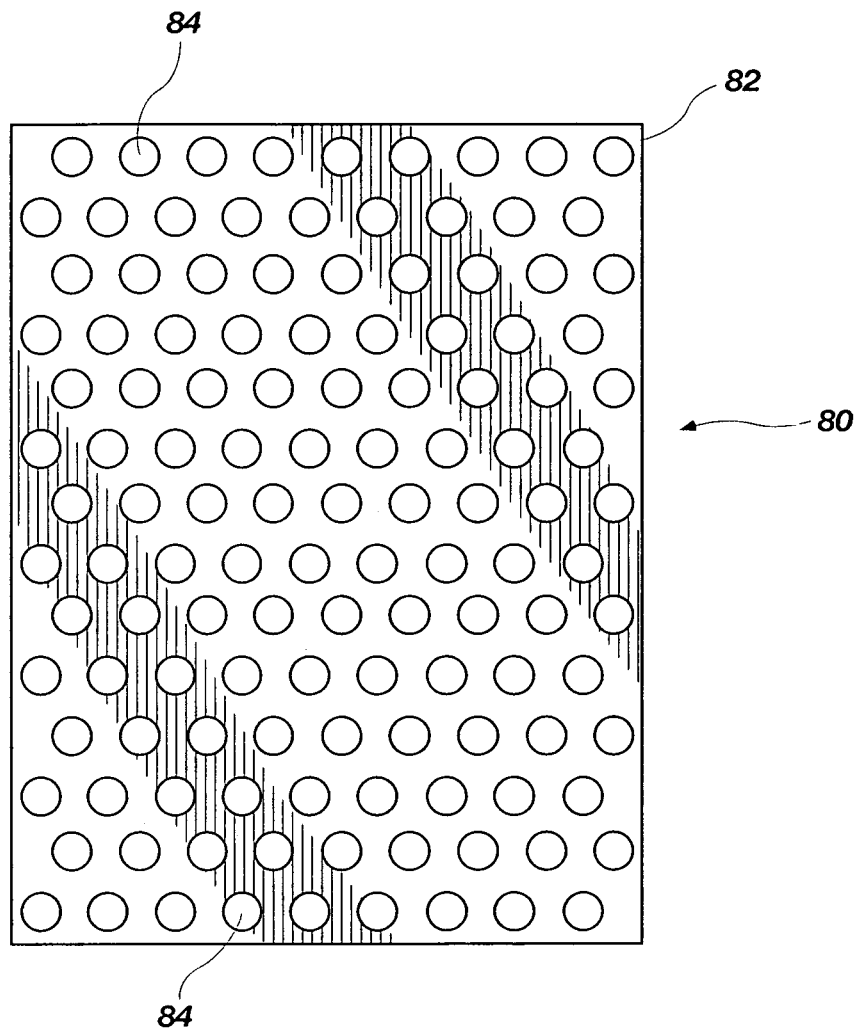
FIG. 8 depicts the template for use with the system described herein.
Figure 9:
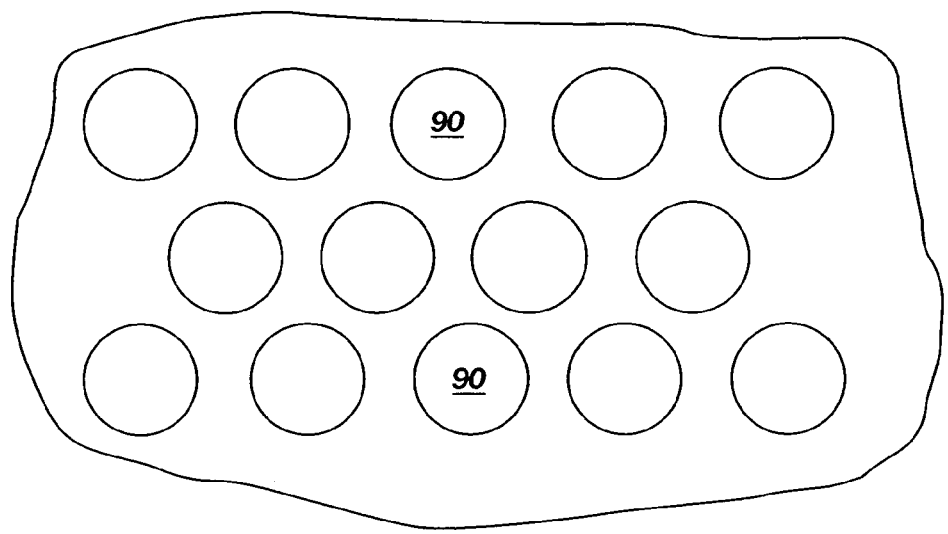
FIG. 9 is a cartoon depicting placement of the dots on the first treatment session.
Figure 10:
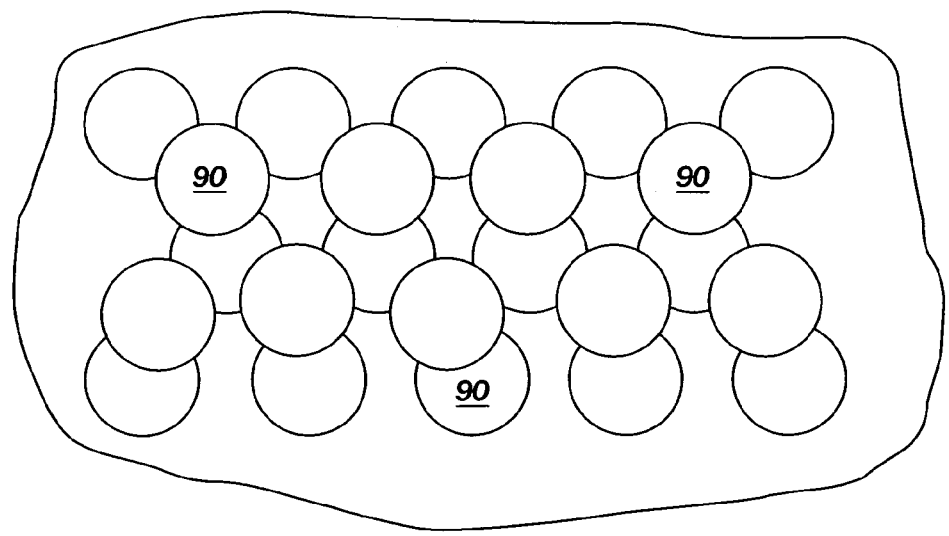
FIG. 10 is a cartoon depicting placement of the dots on the second treatment session.
Figure 11:
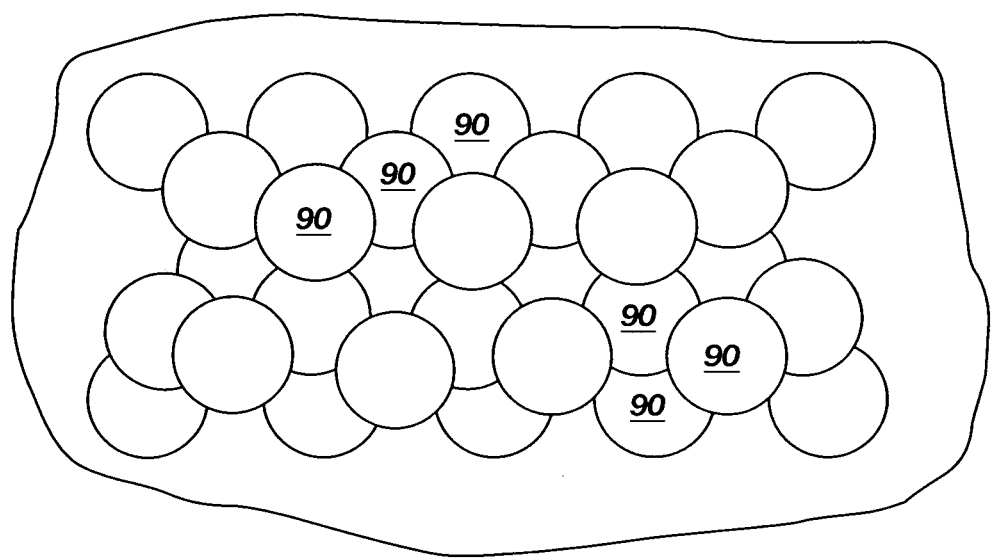
FIG. 11 is a cartoon depicting placement of the dots on the third treatment session.

The template 80 is provided to ensure that the treatment dots are of the correct size and are spaced the correct distance apart. A template (FIG. 8) is preferably made of a thin, flexible material that can be easily cut by scissors (e.g., thin cardboard, paper, polymeric material, plastic, or thin metal). An associated backing 82 is removed from the remainder of the template to expose an adhesive layer and the template is applied to the area of tattoo to be treated. The template may be cut with a pair of scissors to the optimum size desired. Using a skin marker and after placement onto the tattoo, apertures 84 in the template 80 are filled in leaving marking ink on the surface of the tattoo in the form of "dots" (FIGS. 9-11). When the dots are filled in with the ink from the skin marker, the template 80 is removed from the skin and discarded. The resulting treatment dots 90 (and the apertures in the template) are typically three (3) to six (6) mm, preferably five (5) mm, in diameter and are spaced from two (2) to five (5) millimeters, preferably three (3) mm, apart in every direction. The portion of the template that adheres to the subject's skin is typically white or transparent.

Preferably, a treatment session aims to cover the whole area of the tattoo. It is thus preferred that a pattern of dot placement be used that maximizes the effect of the first treatment session, and minimizes the total number of sessions required. Applying around the tattoo during the first session to the extent possible is preferred. If the whole area of the tattoo can be treated with circles in one visit, it is theoretically possible to completely treat most tattoos in four (4) or five (5) adequately spaced sessions.

The template ensures that the dots are made in lines and that each treated circle is approximately five (5) mm in diameter with three (3) mm gaps in between (see, e.g., FIG. 9). In subsequent treatments (see, e.g., FIGS. 10 and 11), the template 80 is offset or "shifted" to cover previously untreated areas. Such a procedure means that once the treated areas have healed and matured, a further, e.g., five (5) mm diameter dot placed between two pre-existing treated areas will overlap them by at least one (1) mm each side (FIG. 10).

The use of the template 80 enables accurate placement of the treatment circles 90 and a much easier removal strategy for the second (FIG. 10) and subsequent (e.g., FIG. 11) sessions. Position the template 80 and use the marker pen to fill in the circles. Approximately six (6) minutes are allowed for the marker ink to dry before commencing treatment.

The hand piece wand 50 is held as if holding a pen with the index finger comfortably placed upon or near to the fluid delivery tube/needle assembly connector. The other hand may be used to spread or stretch the area of skin to be treated. Non-latex textured gloves may improve traction.

The treatment wand should be running before application to the skin. A maximum motor speed of 150 cycles is typically used. The hand piece wand 50 is gently applied to the skin, perpendicular to it and applied so that the needles are penetrating up to the hilt of the needle assembly after setting the needle depth.

A circular motion is commenced, gently at first, to start the de-epithelialization, gradually spiraling outward until the marking ink has been removed to create, e.g., a five (5) mm zone of treatment corresponding to the dot 90. It is advisable to spiral out approximately five (5) complete rotations before reversing the direction of rotation and spiraling back to the center.

The area may be evenly de-epithelialized so as not to leave a central peak of epithelialized skin. Each circle completed takes approximately 12 seconds.

FIG. 9 depicts the placement of dots during the first treatment session. The physician starts at the edge of the tattoo design furthest away and work back towards himself Once the physician has created a row of dots across the full width of the tattoo design, a second row underneath is commenced.

FIG. 10 depicts the placement of dots about the tattoo during the second treatment session. The physician continues in this manner until the whole area of the tattoo design is covered. (See, FIG. 11).

As the cosmetic process/treatment progresses, a little light bleeding from each of the treatment dots may be experienced. However, this soon stops as it is coagulated by the fluid and each dot takes on a dark appearance. The dots are surrounded by a wheal and flare reaction which swells their margin. Each dot resembles a dark, pit-like structure.

About four hours after creation of the wound dots, a solution such as BIAFINE® topical emulsion (Ortho Dermatologics, USA) may be applied to assist in wound healing. Prophylactic antibiotics (e.g., a broad spectrum cephalosporin) may also be utilized according to manufacturer instructions to prevent infection of the wound dot. The application of, e.g., BIAFINE® may be repeated a few days post treatment.

Silicone gel sheeting (e.g., BIODERMIS® or EPI-DERM®) may be used to prevent hypertrophic scarring. Typically, the silicone gel sheeting is worn for twelve (12) to twenty-four (24) hours a day for eight (8) to twelve (12) weeks.

As subsequent treatment sessions are performed, it is reasonable to make any dot less than the preferred five (5) mm in diameter and to modify the shape of the treatment zone according to what the user sees. For example, a thin line tattoo can be removed by "scoring" the line out to the appropriate depth, using a back and forth motion of the hand piece. Letters and words can be managed in this fashion. However, a "dot" pattern may ultimately camouflage such a line better, blending it into surrounding skin.

There are often two phases in the healing of the resulting wound. Within 24 hours, the treated zones form a hard capped mini eschar. The initial eschar phase lasts from one to three weeks depending upon the relative depth of the treated zones. When the eschar separates, there may be a small moist wound that forms a secondary, blood-product-based true scab. All wounds should be healed within three weeks. The wound should be healed as soon as possible in order to minimize the chance of poor scar formation.

Modern wound management typically relies upon moist healing techniques. In this respect, the management of the instant wound is counter-intuitive. The treated area is initially covered with a dry dressing and then may either be kept lightly covered during the day or exposed. Any dressing during this phase is merely to protect the area from observation or to prevent it from rubbing on clothing and thus becoming more inflamed. Attempts to use occlusive dressing techniques in the early phase, unless these are changed every 24-48 hours, may result in an offensive discharge and superficial infection. Once the initial eschars have separated, a moist healing technique is appropriate.

After all eschars have separated, there will be erythematous dots representing freshly re-epithelized, thinner dermis. These areas are further managed to reduce the chance of hypertrophic scarring and to minimize the time interval between treatment sessions.

It should be emphasized to the subject that this second phase of management is an intrinsic part of the cosmetic process, with which they must be compliant or risk a poor result. The best way to achieve this is to use silicone sheeting in the same manner as surgeons manage other cosmetic procedure scars. Various brands of silicone sheeting are available. The best are adhesive, re-usable, and have a cloth backing on one side to prevent them sticking to clothes. Silicone gels applied topically from a tube do not have the same efficacy, but may be a "better than nothing" solution if the subject cannot tolerate a silicone sheet.

Silicone sheets should be worn 24 hours, being removed only for bathing and social events. They should be kept in place until the treatment dots have become pale and remain flat with respect to the surrounding skin. Consistent use of gel sheeting can reduce the occurrence hypertrophic and keloid scarring.

Subjects heal at different rates and their treatment "dots" settle in a similar fashion. It is advisable to wait to perform a further treatment until the erythema in each dot is settling and it remains flat. In short, it must have sufficiently matured as a wound to permit a further dot to be made adjacent and partially overlapping it.

The interval between treatment sessions should not be rushed. It may be longer than is required between laser sessions. If the interval is shortened too much, the degree of additional inflammation in the treatment zone may provoke a hypertrophic scar.

A typical follow-up protocol includes a treatment session, inspect at three weeks to ensure healing and commence scar prevention, see at two months to determine whether further treatment can take place (if not see at monthly intervals until treatment is possible), determine at any time if any untoward event or upon request.

In certain embodiments, a neutralizing pigment, wherein the neutralizing pigment matches the subject's skin color adjacent the tattoo to be removed.

As can be seen, the system is readily applicable to a method of doing business. In such a method, users (e.g., physicians, nurses, registered and properly trained cosmeticians, etc.) enroll in the program, and are trained to operate the described system and be aware of the advantages and drawbacks of the system, especially as it relates to particular users. The equipment and supporting materials for performing the system are obtained from the system owner (e.g., by lease, sale, license, etc.)

After the trained health care professional begins practicing the system, e.g., a royalty is paid back to the system owner dependent upon the number of procedures performed. Geographical territories for using the system might be licensed to the user. Management of the system and associated business method can be accomplished with the aid of the internet for information, communication, and referrals, electronic fund transfers between the user and the system owner, remote review of digital images for consulting services to determine the best method of treatment for a particular tattoo, and continuation of a tattoo removal in another geographical territory by another enrolled user/healthcare professional.

In such an embodiment, a computer system can be adapted to help manage the practice of the user (e.g., for storing subject records and photographs, for reporting requirements back to the system owner, for purchases of additional materials such as the eschar-inducing materials, needle cartridges, and syringes).

After being apprised of the instant disclosure, those of ordinary skill in the art will be able to make and use the described system by obtaining and/or modifying commercially available devices and components.

What is claimed is:

1. A method of removing a tattoo from a subject of the type involving delivering a eschar-inducing material into the area of skin associated with the tattoo, wherein the improvement comprises:
  utilizing a template to determine the placement of the eschar-inducing material into an area of skin, the template comprising:
    a first layer having a first side and a second side, the first layer made of a flexible, cuttable material and having uniformly spaced circular apertures, each circular aperture thereof having a constant diameter of between about three (3) and about six (6) millimeters, and spacing of from about three (3) to about five (5) millimeters therebetween, wherein the second side thereof has an adhesive associated therewith for removable adhesion to a subject's skin, and
    a second, cuttable removable layer covering the second side and preserving the adhesiveness thereof so that upon removal of the second layer from the first layer, adhesive is exposed for removable application of the first layer to the subject's skin about a tattoo placed thereon, wherein the circular apertures open above the subject's skin,
  utilizing the template comprising:
    cleaning a skin area of the subject at and around a tattoo to be removed,
    shaping the template to accommodate the tattoo,
    removing the second layer from the first layer of the template,
    placing the first layer of the template adhesive side down upon the tattoo,
    marking dots upon the tattoo through said apertures in the template,
    removing the template, and
    delivering, with at least one needle, eschar-inducing material into the tattoo at the dots, so that the eschar-inducing material disrupts local skin cells and liberates pigments of the tattoo from the subject's skin, thus dissolving pigments associated with the tattoo, which pigments are coagulated within an eschar for later removal.

2. The method according to claim 1, wherein, after allowing time to heal, the method is repeated with the template's placement offset to a position where the eschar-inducing material is placed into an area adjacent to the skin previously treated and not in the skin previously treated, but still containing pigments associated with the tattoo.

3. The method according to claim 1, further comprising utilizing a test patch on the tattoo.

4. The method according to claim 1, wherein the eschar-inducing material is delivered at a continuous flow at a pressure greater than the pressure provided just by gravity.

5. The method according to claim 4, wherein the eschar-inducing material is delivered with the aid of a pump.

6. The method according to claim 1, further comprising:
  redelivering eschar-inducing material fluid to the subject's skin after from about eight (8) to about sixteen (16) weeks.

7. A method of removing a tattoo from a subject of the type involving delivering a eschar-inducing material into the area of skin associated with the tattoo, wherein the improvement comprises:
  utilizing a template to determine the placement of the eschar-inducing material into the area of skin, the template comprising:,
    a first layer having a first side and a second side, the first layer made of a flexible, cuttable material and having uniformly spaced circular apertures, each circular aperture thereof having a constant diameter of between about three (3) and about six (6) millimeters, and spacing of from about three (3) to about five (5) millimeters therebetween, wherein the second side thereof has an adhesive associated therewith for removable adhesion to a subject's skin, and
    a second, cuttable removable layer covering the second side and preserving the adhesiveness thereof so that upon removal of the second layer from the first layer, adhesive is exposed for removable application of the first layer to the subject's skin about a tattoo placed thereon, wherein the circular apertures open above the subject's skin,
  wherein the template is utilized by:
    cleaning a skin area of the subject at and around a tattoo to be removed,
    shaping the template to accommodate the tattoo,
    removing the second layer from the first layer of the template,
    placing the first layer of the template adhesive side down upon the tattoo,
    marking dots upon the tattoo through said apertures in the template,
    removing the template, and
    delivering, with at least one needle, eschar-inducing material into the tattoo at the dots, so that the eschar-inducing material disrupts local skin cells and liberates pigments of the tattoo from the subject's skin, thus dissolving pigments associated with the tattoo, which pigments are coagulated within an eschar for later removal, wherein the eschar-inducing material is delivered at a continuous flow at a pressure greater than the pressure provided just by gravity, and wherein the eschar-inducing material is delivered with the aid of a pump.

8. The method according to claim 1, further comprising selecting the diameter of each of the circular apertures of the template to equal five (5) mm, wherein the circular apertures are spaced three (3) mm apart in each direction.

* * * * *